(12) United States Patent
Silay et al.

(10) Patent No.: US 10,232,168 B2
(45) Date of Patent: Mar. 19, 2019

(54) SYSTEM FOR ACTIVE SKULL REPLACEMENT FOR BRAIN INTERFACE AND METHOD OF USING THE SAME

(71) Applicant: ECOLE POLYTECHNIQUE FEDERALE DE LAUSANNE (EPFL), Lausanne (CH)

(72) Inventors: Kanber Mithat Silay, Rotkreuz (CH); Gürkan Yilmaz, Chavannes-près-Renens (CH); Catherine Dehollain, Romanel-sur-Morges (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 340 days.

(21) Appl. No.: 15/193,218

(22) Filed: Jun. 27, 2016

(65) Prior Publication Data
US 2017/0368330 A1    Dec. 28, 2017

(51) Int. Cl.
*A61N 1/00* (2006.01)
*A61N 1/05* (2006.01)
(Continued)

(52) U.S. Cl.
CPC .......... *A61N 1/0539* (2013.01); *A61B 5/0006* (2013.01); *A61B 5/0031* (2013.01);
(Continued)

(58) Field of Classification Search
CPC ............................ A61N 1/0539; A61B 5/0006
(Continued)

(56) References Cited

U.S. PATENT DOCUMENTS 7,212,864 B2    5/2007  Wahlstrand et al.
7,346,391 B1    3/2008  Osorio et al.
(Continued)

OTHER PUBLICATIONS

Carrette, Evelien, et al. "Predictive factors for outcome of invasive video-EEG monitoring and subsequent resective surgery in patients with refractory epilepsy." Clinical neurology and neurosurgery 112.2 (2010): 118-126.
(Continued)

*Primary Examiner* — Nadia A Mahmood
(74) *Attorney, Agent, or Firm* — Andre Roland S.A.; Nikolaus Schibli (57) ABSTRACT

An active skull replacement system including an implant having an area A, an upper surface, and a bottom surface, adapted to be implanted at least in part into a skull of a subject so to substitute a portion of the skull, the bottom surface arranged to face at least in part a cranial cavity, and having a first wireless bidirectional data communication device, a device operably connected to the bottom surface of the implant, the device adapted to at least one of stimulate a physiological response and record a physiological parameter of the subject, and an external reader adapted to be placed on the scalp of the subject and including a second wireless bidirectional data communication device configured to communicate with the first wireless bidirectional data communication device of the implant to operate the device, wherein the external reader and the implant are fixed and aligned among each other through a magnetic device.

12 Claims, 7 Drawing Sheets

(51) Int. Cl.
*A61B 5/00* (2006.01)
*A61B 5/0476* (2006.01)
*A61N 1/36* (2006.01)
*A61N 1/378* (2006.01)
*A61N 1/372* (2006.01)

(52) U.S. Cl.
CPC .......... *A61B 5/0476* (2013.01); *A61B 5/4064* (2013.01); *A61B 5/6868* (2013.01); *A61N 1/0531* (2013.01); *A61N 1/0534* (2013.01); *A61N 1/36082* (2013.01); *A61N 1/36139* (2013.01); *A61B 5/0002* (2013.01); *A61B 5/4082* (2013.01); *A61B 5/4094* (2013.01); *A61B 5/4815* (2013.01); *A61B 5/4836* (2013.01); *A61N 1/3787* (2013.01); *A61N 1/37217* (2013.01)

(58) Field of Classification Search
USPC .......................................................... 607/2
See application file for complete search history.

(56) References Cited

U.S. PATENT DOCUMENTS

| | | | |
|---|---|---|---|
| 8,165,684 | B2 | 4/2012 | Putz et al. |
| 9,084,901 | B2 | 7/2015 | Wahlstrand |
| 2001/0051819 | A1 | 12/2001 | Fischell et al. |
| 2004/0176817 | A1 | 9/2004 | Wahlstrand et al. |
| 2005/0113744 | A1 | 5/2005 | Donoghue et al. |
| 2007/0255338 | A1 | 11/2007 | Wahlstrand |
| 2009/0149913 | A1* | 6/2009 | Putz .................... A61B 5/0017 607/45 |

OTHER PUBLICATIONS

Hamer, H. M., et al. "Complications of invasive video-EEG monitoring with subdural grid electrodes." Neurology 58.1 (2002): 97-103.

Kilinc, Enver G., et al. "A remotely powered implantable biomedical system with location detector." IEEE transactions on biomedical circuits and systems 9.1 (2015): 113-123.

Reichert WM, editor. Indwelling Neural Implants: Strategies for Contending with the In Vivo Environment. Boca Raton (FL): CRC Press/Taylor & Francis; 2008, Chapter 3

Silay, Kanber Mithat, Catherine Dehollain, and Michel Declercq. "Inductive power link for a wireless cortical implant with two-body packaging." IEEE Sensors Journal 11.11 (2011): 2825-2833.

Yilmaz, Gürkan. "Wireless Power Transfer and Data Communication for Intracranial Neural Implants Case Study." (2014).

Silay, K. M. (2012). Remotely powered wireless cortical implants for brain-machine interfaces, Ph.D. Thesis No. 5286 of Ecole Polytechnique Federale de Lausanne (EPFL).

Silay, K. M., Dehollain, C., & Declercq, M. (2013). A closed-loop remote powering link for wireless cortical implants. IEEE Sensors Journal, 13(9), 3226-3235.

* cited by examiner

SYSTEM FOR ACTIVE SKULL REPLACEMENT FOR BRAIN INTERFACE AND METHOD OF USING THE SAME

TECHNICAL FIELD

The present invention generally relates to the field of medical devices, more particularly it pertains to a skull replacement implant incorporating wirelessly-actuated electronic devices for medical purposes.

DISCUSSION OF THE BACKGROUND ART

Recording neural activities plays an important role in numerous applications ranging from brain mapping to implementation of brain-machine interfaces (BMI) to recover lost functions or to understand the mechanisms behind the neurological disorders such as essential tremor, Parkinson's disease and epilepsy. It also constitutes the first step of a closed-loop therapy system which additionally employs a stimulator and a decision mechanism. Such systems are envisaged to record neural anomalies and then stimulate corresponding tissues to cease such activities. Methods for recording the neural signals have evolved to its current state since decades, and the evolution still goes on.

Current clinical practice in recording electrical activities of the brain is dominated by electroencephalography (EEG) which is a non-invasive procedure performed along the scalp. Another type of EEG, intracranial EEG (iEEG; also known as electrocorticography (ECoG)) is an invasive procedure which is performed by placing an electrode matrix (or array) onto the cortex following craniotomy. Intracranial EEG is, for instance, employed for epileptic focus localization prior to a respective surgery which is performed to treat certain types of epilepsy.

Currently, iEEG is performed by using electrode arrays composed of millimeter-sized passive electrodes. See Carrette E. et al., Clinical Neurology and Neurosurgery, 112(2): 118-126, 2010. Neural signals acquired via these electrodes are transferred to an external recording device via transcutaneous wires. However, the wired connection through the skull during the monitoring period increases the risk of the cerebrospinal fluid (CSF) leakage, or worse, infection of the CSF. So far, all the implantation procedures are achieved using transcutaneous wired devices, associated with potential serious complications in up to 25% of cases, such as intracranial infections or CSF leakage. See Hamer H. M. et al., Neurology, 58(1):97-103, January 2002. Finally, patients are permanently connected to a recording station through multiple connecting cables, leading to decreased comfort and autonomy. This situation reduces the patient mobility and affects psychological state of the patient and more importantly limits the monitoring period. Sealing the craniotomy area up is anticipated to eliminate or at least minimize these risks.

The demand from neural systems increases continuously in terms of quality and quantity of extracted information with the improvements in the microsystems and microelectronics. This demand drives the technology from external recording systems to in-vivo recording systems. As new technological developments take place, so does the opportunity to improve current designs or performance, decrease power requirements or cost, and/or minimize complications associated with chronic implantation. Implanted neural recording systems are expected to offer better spatial and temporal resolution, thanks to implantable microelectrodes and on-site processing microelectronics.

Implantable biomedical devices usually require an isolated volume from the surrounding tissues to prevent the cross-interaction between the device and the tissues. This isolation, however, should not deteriorate the performance of the device. Independent of the location of the implantation, the isolated volume is to be provided by the human body volume. Therefore, a subtractive process is to be performed at the location where the implant is placed. Specifically, for the brain implants, the volume is usually obtained by forming a recess on/inside the cranium. It should be noted that, generally, it is required to implant the biomedical device as close as possible to the point-of-interest. See U.S. Pat. Pub. No. 2005/0113744. As another note, the dimensions of the recess which will contain the implantable device is limited from the upper bound by the physiological limits of the human anatomy and from the lower bound by the content of the device, for instance, electrical and mechanical parts.

U.S. Pat. Nos. 7,212,864 and 9,084,901 proposed a method to implant a biomedical device into the head of a patient. They suggest placing some modules that are completely covered by an overmold between the cranium and the scalp, while the rest of the modules that are partially covered with another overmold into a recess in the cranium. The purpose is to distribute the parts of the implant in such a way that most of the implant volume is to be placed into a recess in the cranium, and therefore, less implant volume is required between the cranium and the scalp. However, these approaches are uncomfortable in case the module placed between the cranium and the scalp should be replaced or removed, and could be aesthetically unpleasant.

A further recent approach relates to drilling a Burr hole and implant the biomedical device therein. Silay K M et al., Sensors Journal, IEEE, vol. 11, no. 11, pp. 2825-2833; Wireless Power Transfer and Data Communication for Intracranial Neural Implants Case Study: Epilepsy Monitoring, Ph. D. thesis by Gürkan Yilmaz. By this way, the performance of the system has been improved without sacrificing from the surface area of the Burr hole. This approach however provides little space for placing a plurality of active devices for monitoring or influencing brain activity, for adapting several (bidirectional) data communication components or (wirelessly-driven) power supply and, importantly, for managing the thermal burden generated by the active elements of an implant. See Patrick D. Wolf, Thermal considerations for the design of an implanted cortical brain-machine interface (BMI). In William M Reichert, editor, Indwelling neural implants: Strategies for contending with the in vivo environment. CRC Press, Boca Raton (Fla.), 2008).

Some additional patent applications and publications, including U.S. Pat. Nos. 7,346,391, 8,165,684, and U.S. Pat. Pub. Nos. 2001/0051819, 2004/0176817 and 2007/0255338, provide different scenarios concerning cerebral implantable medical devices or brain-machine interfaces. Especially in this latter case, none of those documents addressed or focused on some of the practical problems arising during the operation of said devices, namely the need of an as much as possible minimally invasive implant for avoiding discomfort of the patient, the optimization of the power supply of the implanted device and/or of the bidirectional data communication with external systems so to avoid external structures such as wired cables or catheters, and at the same time the need of dissipating the heat load generated during operation of an active implant. Accordingly, despite all the advancements in the field of skull replacement and brain interfaces, additional and more advanced solutions are still necessary and desired.

SUMMARY

Bearing in mind all the drawbacks of the prior art approaches, and in order to address and overcome them, an optimized solution has been developed for a brain-machine interface system. The system envisages an active skull implant intended for replacement of a portion or a major part of the skull of a subject (human or animal). The implant is active in that it comprises functional electronic devices, which consume power and process information, adapted for stimulating a physiological response and/or record a physiological parameter of the subject. The implant is functionally coupled with an external reader device located outside the body of the subject and on, or very close to, the scalp thereof, in order to complement the functions of implant. External reader can be used to send power and information to the implant, collect and/or process information recorded from it and/or communicate with a remote host. The remote host is a computer-based device operably connected to the implant and/or to the external reader and adapted for sending and/or receiving information from these devices and process this information for diagnostic or emergency related situations.

The particularity of the system according to one aspect of the invention preferably relies in three main aspects:

(1) the complete wireless nature of the data communication between the active implant and the external reader. Thanks to the optimization design of the components of the system, wired connections between an implanted device and an external one is avoided, thus drastically reducing or eliminating post-surgery complications such as the risk of infections or of cerebrospinal fluid (CSF) leakage e.g. during a monitoring period. Moreover, by implementing wireless connection of the system with a remote host instead of using wired connection, the subject mobility and his/her psychological state would ameliorate, together with his/her comfort and autonomy;

(2) the structure of the active implant, in terms of area/volume thereof, materials used and its architecture is adapted to improve the dissipation of the heat generated by telemetric devices, power supplies, Eddy currents and the like; and (3) the presence of a simple an elegant system for easily fixing and removing the external reader from the subject, also permitting an easy way to reciprocally align certain component of both the reader and the skull implant when needed. This feature is somehow linked to point (1) above.

Preferably, in some instance, such for example in the presence of inductive elements for supplying power or charging the batteries of the implant (e.g., solenoid coils), or in the presence of antennas for bidirectional data transfer between the reader and the implant, a correct alignment is needed for the optimal functioning of the system. However, when a non-fixed or non-fixable external device as part of said system is used, said alignment could result particularly troublesome and tricky. The various components of the system, i.e., the active skull implant and the external reader, have been designed for comprising means for magnetically pairing said components among them, in order to conveniently and efficiently coupling and fasten/unfasten the external reader on demand while reducing physical constraints.

According to one aspect of the present invention, preferably an active skull replacement system is provided. Preferably, the system comprises an implant having an area A, an upper surface, and a bottom surface, adapted to be implanted at least in part into a skull of a subject so to substitute a portion of the skull, the bottom surface arranged to face at least in part a cranial cavity, and having a first wireless bidirectional data communication device, and a device operably connected to the bottom surface of the implant, the device adapted to at least one of stimulate a physiological response and record a physiological parameter of the subject. Moreover, the system further preferably includes an external reader adapted to be placed on the scalp of the subject and including a second wireless bidirectional data communication device configured to communicate with the first wireless bidirectional data communication device of the implant to operate the device, wherein the external reader and the implant are fixed and aligned among each other through a magnetic device.

In a preferred embodiment, area A of the implant of the system is adapted to dissipate the heat generated by at least one of the implant and the device operably connected to the bottom surface of the implant. Also, the system includes the first device for wireless bidirectional data communication of the implant including an antenna, and the second device for wireless bidirectional data communication of the external reader including an antenna.

In a preferred embodiment, the antennas are concentrically aligned among them through the magnets in the system In a preferred embodiment, the external reader includes a device for remote powering of the implant.

In a preferred embodiment, the device for remote powering is exerted via magnetic coupling of at least one solenoid coil or at least one antenna operably placed in both the implant and the external reader.

In a preferred embodiment, the system is characterized in that the at least one solenoid coil or the at least one antenna in each component of the system independently are in an orthogonal orientation.

In a preferred embodiment, the system is characterized in that area A of the implant is $((\sqrt{N}+(\sqrt{N}-1))^2) \times x^2$, wherein x is the diameter of an antenna and N is the number of antennas.

In a preferred embodiment, the system is characterized in that the at least one device operably connected to the bottom surface of the implant is an electrocorticography electrode or an array thereof, active/passive microelectrode arrays with stimulation/recording capabilities, a deep brain stimulation electrode or an array thereof, a drug delivery device, a chemical sensor, a temperature sensor or a pressure sensor.

In a preferred embodiment, the system further comprises a computer-based remote host operably connected to the implant and/or to the external reader and adapted for communicating with them and/or for collecting, sending, storing and/or processing information concerning a physiological response and/or a physiological parameter of a subject.

Another object of the present invention relates to a method to use of the above system for the treatment, diagnosis, monitoring and/or prevention of a disorder of the Central Nervous System (CNS).

The above and other objects, features and advantages of the present invention and the manner of realizing them will become more apparent, and the invention itself will best be understood from a study of the following description with reference to the attached drawings showing some preferred embodiments of the invention.

BRIEF DESCRIPTION OF THE SEVERAL VIEWS OF THE DRAWINGS

The accompanying drawings, which are incorporated herein and constitute part of this specification, illustrate the presently preferred embodiments of the invention, and together with the general description given above and the detailed description given below, serve to explain features of the invention.

Herein, identical reference numerals are used, where possible, to designate identical elements that are common to the figures. Also, the images in FIGS. 1-2 are simplified for illustration purposes and may not be depicted to scale.

DETAILED DESCRIPTION OF THE SEVERAL EMBODIMENTS

In general, a system comprising an implantable active device for implantation into an aperture formed in the skull of a subject is provided, and a method of using the same. The term "subject" as used herein refers to mammals. For example, mammals contemplated by the present invention include human, primates, domesticated animals such as cattle, sheep, pigs, horses, laboratory rodents and the like. The implant can have any suitable shape and in preferred embodiments it is substantially a parallelepiped having a flat appearance, with an upper surface and a bottom surface. The implant is construed to be implanted at least in part into the skull of a subject so to substitute a portion of said skull. Generally speaking, the implant is placed into a naturally present cranial aperture. due to congenital malformations, accidents and so forth, or an expressly created one, e.g. upon surgical removal of part of the skull. Implantation of said device into a cranial aperture may facilitate cranial implantation of the device, rather than implantation at a subclavicular or other remote location as proposed in the past, so to reduce or eliminate the need for lengthy leads or catheters, and extensive lead tunneling of such leads or catheters. Implantation of an implantable device within a cranial aperture may also facilitate cranial implantation by reducing the profile of the device above the cranium. The reduced profile may be more cosmetically appealing to a patient, and reduce the likelihood of skin erosion of the scalp above the implant site.

One exemplary and non-limiting embodiment of the system according to some aspects of the invention are depicted in FIGS. 1 to 4. For the sake of simplicity and clarity, the several components of the system or combinations thereof are shown in different figures. As said, the active implant 1 is intended to be surgically implanted in substitution of a portion of the skull 200, in close contact with the scalp skin 100 through its upper surface. The implant can be inserted all or in part into the bone, but at least a part of its bottom surface faces or is in direct contact with the cranial cavity 300 and/or its associated structures. Depending on the position, the extension of the substituted skull portion, the cranium profile and so on, the upper and the bottom surface of the implant 1 can have different surface areas. The aperture in the cranium 200 may have a similar shape to that of the implant 1; accordingly, a cross-sectional area at the top of the aperture may be larger than a cross-sectional area at the bottom of the aperture, and larger than a cross-sectional area at the bottom of the implant 1, that is, the implant 1 might have a convex upper surface and a concave bottom surface, in certain embodiments substantially parallel among them. In some embodiments, the implant 1 may be inserted within the aperture by sliding it into the aperture so to direct the implant 1 into the proper location within the aperture. The implant 1 can be surgically secured later on to the skull 200 via any suitable means such as surgical glue 5 (FIG. 1) or screws 6 (FIG. 2) extending through the skull.

Figure 3:
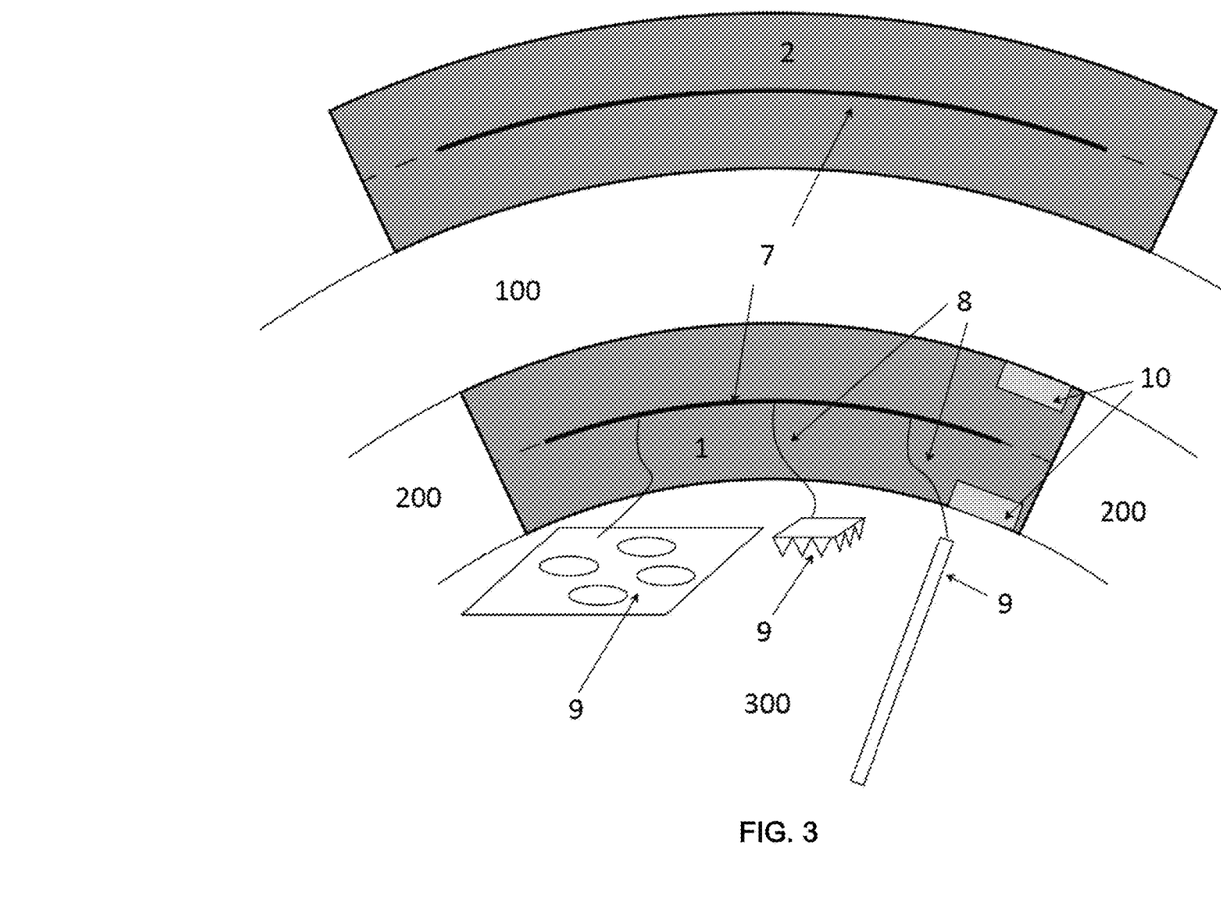
FIG. 3 shows the disposition of active devices and sensors in/on the active implant according to another aspect of the present invention.
Figure 4:
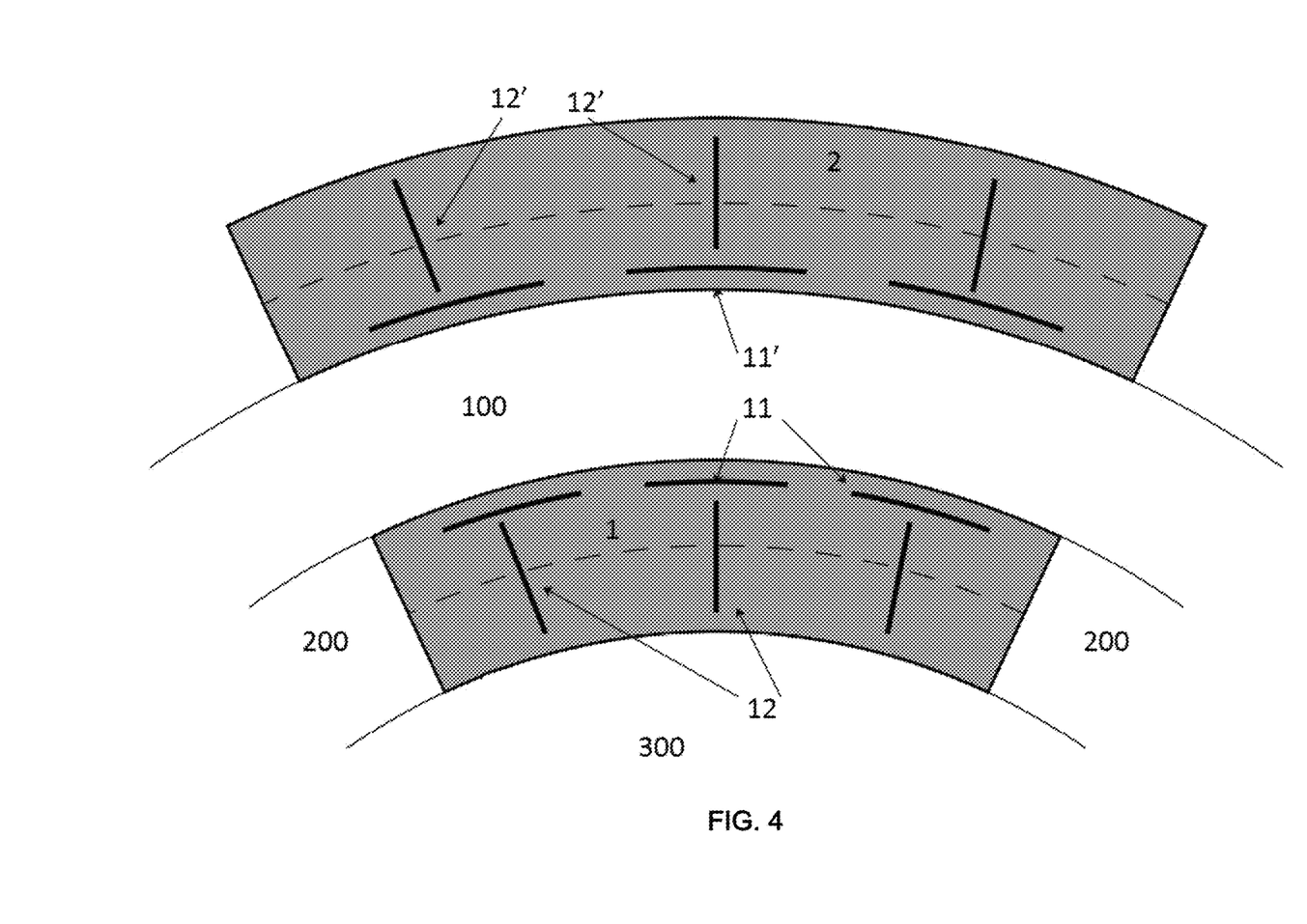
FIG. 4 shows the disposition of solenoid coils and antennas in the active implant and the external reader according to still another aspect of the invention.

The implant 1 integrates a printed board circuit (PCB) 7 shown in FIG. 3 to mechanically support and electrically connect electronic components among them and with a power supply element. The PCB 7 may include many of the components of implant 1 such as analog and digital circuits, e.g., integrated circuit chips and/or a microprocessors. The power supply can be present in the implant 1 in the form of e.g. (rechargeable) batteries (including medical grade ones), a device for remotely receiving power from external sources such as an external reader 2, a remote host 13 or other apparatuses, or combinations thereof. However, according to some aspects of the present invention, the placement in another part of the body of the subject are also possible, such as the chest or abdomen, of an additional wired-connected module if a large battery that cannot be conveniently placed within the cranium.

The remote powering can be implemented with devices that use magnetic coupling, electromagnetic radiations, ultrasounds and/or infrared radiation for wireless and contactless powering. For instance, an antenna 11 or a coil of wire 12 in the active implant 1, formed e.g. of windings of copper or another highly conductive material, may receive energy by magnetic induction from an antenna 11' or an external coil 12' that is suitably placed outside the subject's body but in close proximity to the implant 1, notably in the external reader 2, also for battery recharging purposes. The amount of power received can be adjusted with any kind of closed loop power management system, depending on the power consumption of the components of the implant 1. The implant 1 can also include further components such as data acquisition blocks for collecting information from the devices/sensors (9-10); signal processors for processing the signals and for controlling the blocks in the implant 1 and for handling the communication between these blocks; ambient energy harvesting systems from sources such as vibrations (kinetic energy), thermal gradients or electromagnetic radiation; memory for storing information such as a read-only memory (ROM), random access memory (RAM), flash memory or the like, and so forth. Memory may store program instructions that may be executed by a microprocessor and thereby control the functioning of implant 1 and its associated devices 9.

The implant 1 comprises at least one device 9 (FIG. 3) operably connected to the bottom surface of the implant 1. The device 9 is adapted to directly or indirectly contact the brain 300 or the associated structures (e.g. meninges, capillaries, veins, ventricles and so forth) so to create an interface between the cerebral tissues and the active components of the implant 1 in order to stimulate a physiological response and/or record a physiological parameter of the subject. Device 9 can in some embodiments sense, monitor, quantify or analyze the brain electrical or chemical activity of a subject, predict or detect changes in such brain activity, allow warning, recording or storing data, and/or allow prevention and/or control of undesirable changes in such brain activity, such as the activity changes associated with an epileptic seizure, for example. Moreover, in some embodiments, device 9 can be configured to provide a therapeutic or prophylactic treatment for certain disorders of the CNS, especially of the brain 300 or the associated structures, possibly based on the output of the above detected/monitored parameters. As a consequence, all these operations can be performed in an open-loop (unidirectional) mean, i.e. when devices 9 are only used for sensing, analyzing and/or storing signals from the brain 300, or when an electrical stimulation or other forms of therapy to the brain are provided without receiving or processing brain signals, or they can otherwise executed in a closed-loop (bidirectional) way, i.e. when an output mechanism is activated by the device 9 or other active components of the implant 1 in response to signals received.

For the sake of clarity, the wording "operably connected", "operably connectable" or even "operably connecting" is used herein to reflect a functional relationship between two or more components of a device or a system, that is, such a wording means the claimed components must be connected in a way to perform a designated function. The "designated function" can change depending on the different components involved in the connection; for instance, the designated function of a device operably connected to an active implant, is to operate the function it is suitable for in response to its functional activation exerted by the implant. One of ordinary skill in the art would understand the designated functions of each and every component of the device or the system according to one aspect of the invention, as well as their correlations, on the basis of the present disclosure.

Depending on the envisaged application, its nature and/or its structure, the device 9 can extend on and/or in the brain 300 or the associated structures. For instance, electrocorticography electrodes, active/passive microelectrode arrays with stimulation/recording capabilities, chemical, temperature or pressure sensors 10 and so forth can be distributed towards the cranial cavity or on the surface of the brain 300 so to contact the areas of interest, and possibly inserted at least in part in the tissues. Additionally or alternatively, other devices 9 such as deep brain stimulation electrodes or drug delivery devices can be introduced within specific parts of the brain such as ventricles or nuclei. The devices 9 can be physically placed on the bottom surface of the implant 1 or may extend therefrom by means of wired connections 8, preferably soft ones to reduce the risk of a possible detachment or malfunctioning due to e.g. an accidental impact on the head.

As already briefly outlined, the active implant 1 is constructed in order to facilitate the dissipation of the heat generated for example by telemetric devices and power supplies, and at the same time to allow a functional wireless connection with the external reader 2, both in terms of data and power transfer. For this, the area A and the material used are not chosen arbitrarily, but are adapted in order to fit with these requirements. Concerning the area A, some considerations can be made depending for instance on the number of antennas used for power transfer. For example, being the average human skull thickness around 7 mm and the scalp around 3 mm, maximum coupling, and hence, maximum power transfer efficiency between two loop antennas is achieved at $x\sqrt{2}$ mm separation distance, while x being the diameter of identical loop antennas/inductors. However, practically these antennas have to be placed at least x mm away so that destructive interference is somewhat reduced. Therefore, in one embodiment all the system is characterized in that area A of the implant 1 is $((\sqrt{N}+(\sqrt{N}-1))^2) \times x^2$, wherein x is the diameter of an antenna and N is the number of antennas. If square antennas are used, x must be considered as the side of the antenna.

Turning to the used materials, two combined parameters must be considered: the need of maximizing the heat dissipation due to the heating of device 9 and the obligation of granting wireless power/data transfer between the active implant 1 and the external reader 2. Heat dissipation is a critical issue that must be considered when discussing the power required for an implant. Any electrically powered implanted device dissipates its electrical power as heat or radiates it as electromagnetic radiation. For the heat to be dissipated into the body, the temperature of the implant must be above that of the surrounding tissue. The magnitude of the temperature difference is what is critically important to the safety of the device. In a brain implant consuming hundreds of milliwatts, using a transcutaneous energy delivery system and radio frequency telemetry, the magnitude of the temperature increase and its effects will depend on many factors. The brain has high resting blood flow rates; it receives 20% of the cardiac output despite representing only about 2% of the body's mass. This indicates that there is an extremely high metabolic need in the brain, the heat from which is cleared by the high blood flow.

In this context, the materials used for the production of the implant play a key role. However, as will be evident, a device which is to be implanted inside the body must also satisfy certain biocompatibility and biosafety requirements and standards, as well as certain features regarding bi-directional diffusion barrier, i.e. the quality of physical barrier between the implant and the surrounding tissues and bodily fluids, to maintain and sustain the operation of the implant 1 properly. At the same time, transparency to both magnetic field and electromagnetic radiation, in order to enable lower frequency remote powering with higher frequency wireless data communication, shall be assured. In view of the above, in one embodiment implant 1 is substantially made of a polymeric material embedding at least the active components responsible of data transfer and remote powering such as antennas 11 and solenoid coils 12. Preferred materials, according to one aspect of the present invention, are polydimethylsiloxane (PDMS), Poly(methyl methacrylate), (PMMA), polyimide, epoxy, and Parylene-C, as well as combinations thereof. Such materials are transparent to both magnetic field and electromagnetic radiation, and have good barrier properties. Additionally or alternatively, low temperature co-fired ceramic (LTCC), possessing similar advantages, can be used.

As will be evident to a person skilled in the art, even if polymeric materials helps in distributing the effect of localized heat sources, they do not favour heat dissipation in the surrounding tissue. A solution for facilitating heat dissipation from implant 1 to CNS structures can be adding a conductive structure on the implant's 1 side directly facing the brain cavity. According to one embodiment, implant 1 features a conductive structure on its bottom surface, wherein said structure is in contact with the brain cavity. The structure can be, in one embodiment, a micrometer to millimeter layer of a conductive material such as a metal, preferably a biocompatible metal such as titanium or noble metals as platinum, gold, iridium or silver, combinations thereof and alloys or oxides thereof. The conductive layer can be added during the manufacturing process of the implant through any method known in the art, such as electron beam evaporation, thermal evaporation, sputter deposition, chemical vapor deposition (CVD) or physical vapor deposition (PVD).

The system furthermore includes an external reader 2 including a second communication device for wireless bidirectional data communication with the active components of the active implant 1, including devices 9. As used herein, an "external reader" is a device that forms part of the system and is placed outside the body of a subject. The external reader 2 is construed for being a base station adapted for bidirectional data communication with the implant 1 and optionally with a remote host 13. A peculiarity of the system, as already highlighted, relies in the complete wireless operation of the implant 1. Employing transcutaneous wires to e.g. transfer neural signals have certain drawbacks both from electrical engineering and medical perspectives. Passive macro electrodes acquire analog signals and transmit them through wires to an external base station where amplifiers and analog-to-digital converters are utilized. However, this method reduces the quality of the raw information acquired from the neurons in terms of signal-to-noise ratio (SNR). Moreover, the wires coming out of the scalp increases the risk of cerebrospinal fluid (CSF) leakage, even risk of infection of CSF which may have fatal consequences, and also reduces the patient mobility and comfort. The latter issues may seem less important with respect to former medical risks; however, they, in fact, shorten the monitoring time. Besides, wired connections do not allow life-long implantation which is indispensable for recovering a body function. Wireless data transfer from and to the implant 1 to the external unit 2, therefore, offers solid improvements for e.g. intracranial recording systems. Preferred embodiments of the invention foresee the use of at least one antenna 11' placed in the external reader 2, which is preferably operably placed so to be aligned with a counterpart antenna 11 placed into the implant 1.

The external reader 2 can comprise many of the already mentioned features of the implant 1, such as components for collecting information from the devices/sensors (9-10); signal processors for processing the signals and for controlling the blocks in the implant 1 and for handling the communication between these blocks; ambient energy harvesting systems from sources such as vibrations (kinetic energy), thermal gradients or electromagnetic radiation; memory for storing information such as a read-only memory (ROM), random access memory (RAM), flash memory or the like, and so forth. As for the implant 1, memory may store program instructions that may be executed by a microprocessor and thereby control the functioning of implant 1 and its associated devices 9. The components of the external reader 2 can be operably connected among them via a PCB 7 included within its structure. All or part of these components can be attached, embedded or otherwise coupled into/onto a rigid or soft support; for example, the external reader 2 can be conveniently included into or onto wearable items such as helmets, hats, patches and the like so to be easily placed on demand as close as possible to the implant 1, preferably on the scalp 100 of a subject.

Moreover, in some embodiments, the external reader 2 also comprises means for remote powering of the implant 1. Since implantable batteries cannot always meet with both the size and capacity requirements simultaneously, and ambient energy harvesters are not sufficient for supplying several milliwatts of power continuously, wireless power transfer solutions are therefore appropriate for long-term in-vivo applications such as monitoring of neural signals, in addition or as an alternative to other power supply means. Any technique for remote power transfer can in theory be suitably used in the system, such as inductive coupling, resonant inductive coupling, capacitive coupling, magneto-dynamic coupling and/or microwaves. However, in preferred embodiments, near field wireless transmission of energy are used. This preference is principally linked to the non-radiative nature of the energy transfer, that better fits with other parameters that must be taken into account when a body implant (and particularly an intracranial one) is concerned, especially the temperature management of the active components of the implants that must ensure a maximum tissue temperature elevation of 1° C., corresponding to 40 mW/cm2 power outflux density. For instance, a given DC supply of 1.8V can safely supply a DC current less than 80/1.8 mA for a device having a 1 cm2 top and bottom surface area.

Therefore, among several candidates in wireless power transfer such as ultrasound, electromagnetic radiation, and magnetic coupling, this latter provides the most efficient power transfer in short distances, e.g., in the order of 10 mm, the mean size of the cranium and the scalp of a human being. Moreover, commonly used frequency range (1-10 MHz) for this method allows sufficient bandwidth for data communication for a reasonable number of devices (e.g., electrodes) and a good level of accuracy. In view of the above, in preferred embodiments, the system has an external reader 2 that in turn includes solenoid coils 12' or spiral coils (i.e., antennas 11') for remote powering of the implant 1 exploiting the magnetic coupling principles. Such coils are operably placed into the external reader 2 so to optimize the energy transfer towards the implant's 1 counterparts; in particular, solenoid coils 12-12' present in both the external reader 2 and the implant 1 are aligned along their long axis, or spiral coils 11-11' in both the external reader 2 and the implant 1 are concentrically aligned among them.

Moreover, another coil set, one in the implant 1 and other in the external reader 2, may be employed for data communication between the implant 1 and the external reader 2. Practically and ideally, data communication line carry much less power than power transfer line. Interference of power transfer link on the data communication channel causes degradation of the signal-to-noise ratio (SNR) on the data communication line. The interference between power transfer and data communication channels are maximum when they are concentric and minimum when they are orthogonal to each other. Advantage of such orientation scheme is that less energy-per-bit is required to maintain a desired level of bit-error-rate, which in return decreases temperature elevation, contributed by wireless data communication.

As already outlined, the system is designed to preferably work in a complete wireless mode, for both the bidirectional data transfer and the power supply between the external reader 2 and the implant 1. In this context, the optimization of the transferred signals and electromagnetic waves is crucial for an efficient operation of the system, especially when e.g. said system is intended for continuous monitoring of pathological conditions of a subject and possible counteractions to be performed by active devices 9 based on detections of anomalous physiological parameters. However, the efficient coupling between the components of the system cannot be an easy task for obtaining said optimization.

Particularly, when solenoid coils 12-12' for power transfer and antennas 11-11' for data transmission are included into the functional elements of the system, and designed for being reciprocally well oriented, it is vital that a detachable device for use on demand such an external reader 2 is placed in the correct way on the scalp 100 of the subject; furthermore, not only the correct reciprocal orientation between implant 1 and external reader 2 shall be ensured, but this correct orientation must be granted throughout the entire time period of operation of the system. This can be an uphill struggle when the external reader 2 cannot be somehow fixed and secured on the scalp 100 of the subject with extreme confidence even for long time periods, such as for instance during normal life activities, sleep and the like, or when the subject concerned is a child. Alignment and fixing means can be imagined where spikes, screws or the like protrudes form the implant 1 throughout the scalp 100 up to its surface so to perform as anchor points for an external reader. In another scenario, such as the one envisaged in U.S. Pat. No. 7,346,391, the direct access to an intraosseous implant, and therefore a possible alignment/fixing solution, can be obtained via a tissue pedicle created in the scalp which is attached to and cover the upper surface of the implant. However, as will be evident to a person skilled in the art, such solutions are invasive, at risk of infections and aesthetically unpleasant.

Figure 1:
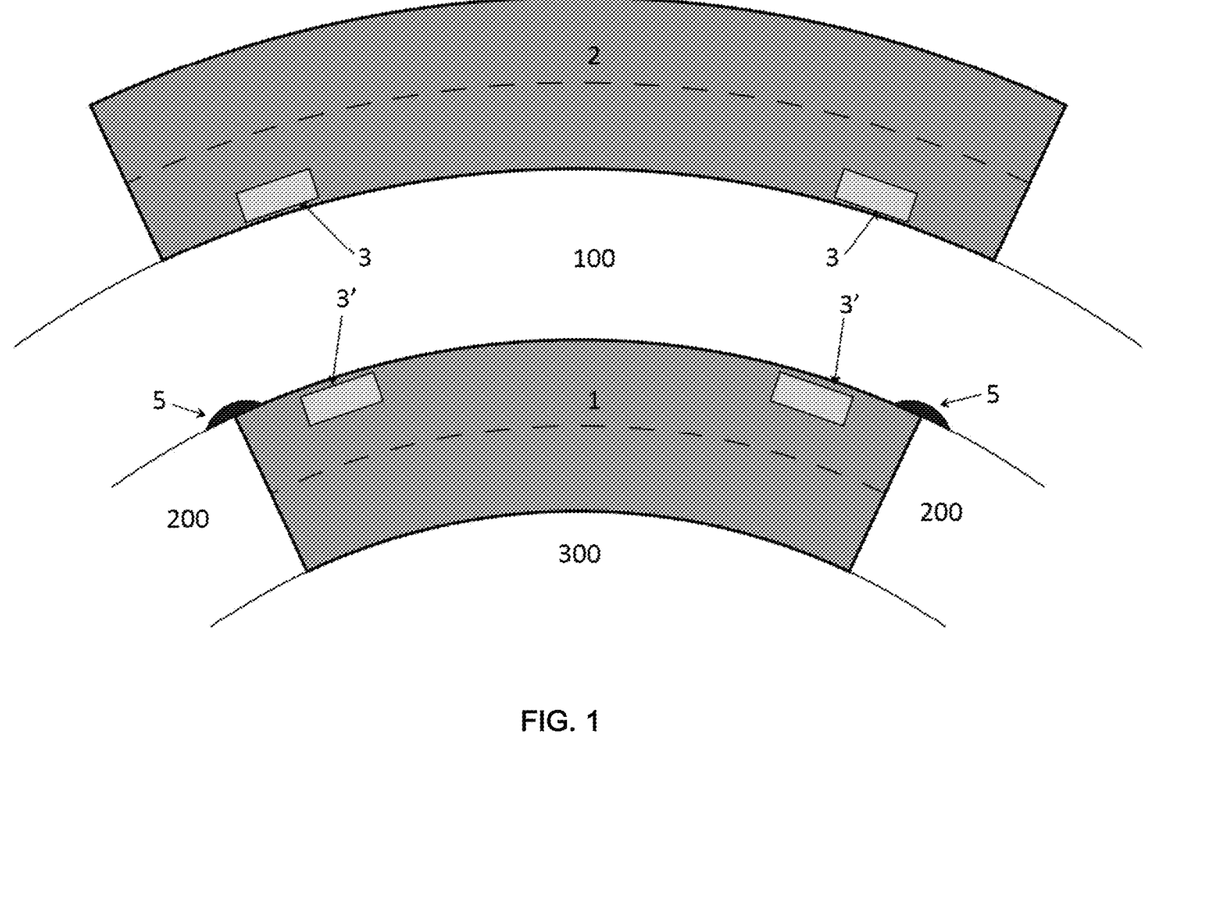
FIGS. 1-2 show two embodiments according to a first aspect of the present invention, in which either a glue (FIG. 1) or screws (FIG. 2) are used to fix the skull replacement implant in a subject.
Figure 2:
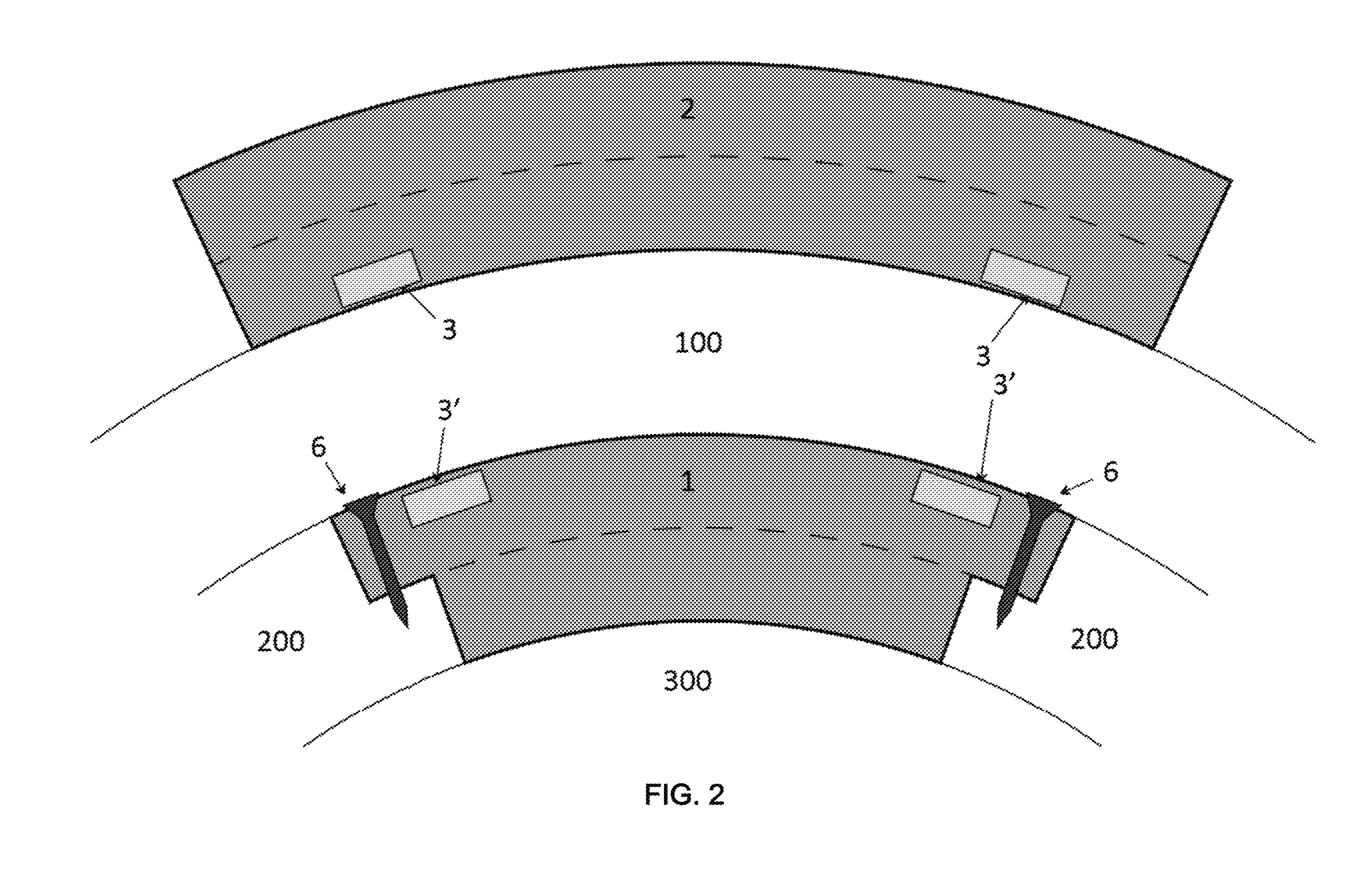
Figure 5:
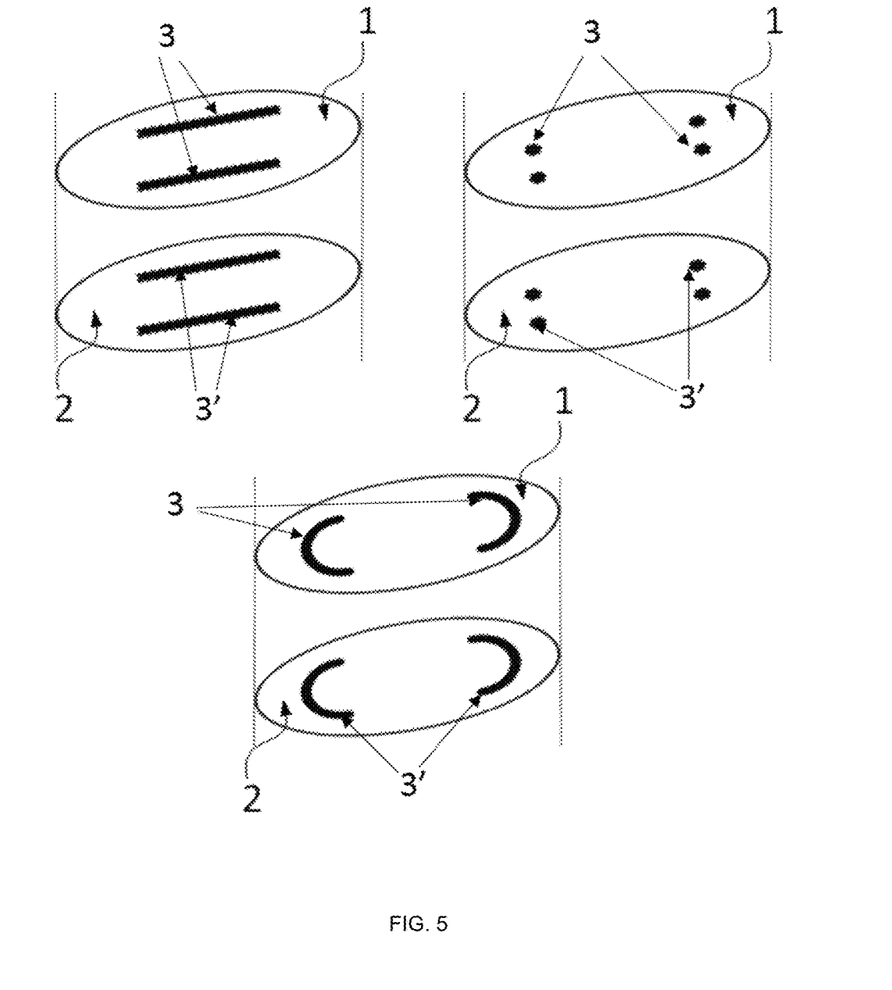
FIG. 5 shows several possible embodiments concerning the positioning and the shape of ferromagnetic elements and magnets on the active implant and the external reader according to yet another aspect of the invention.
Figure 6:
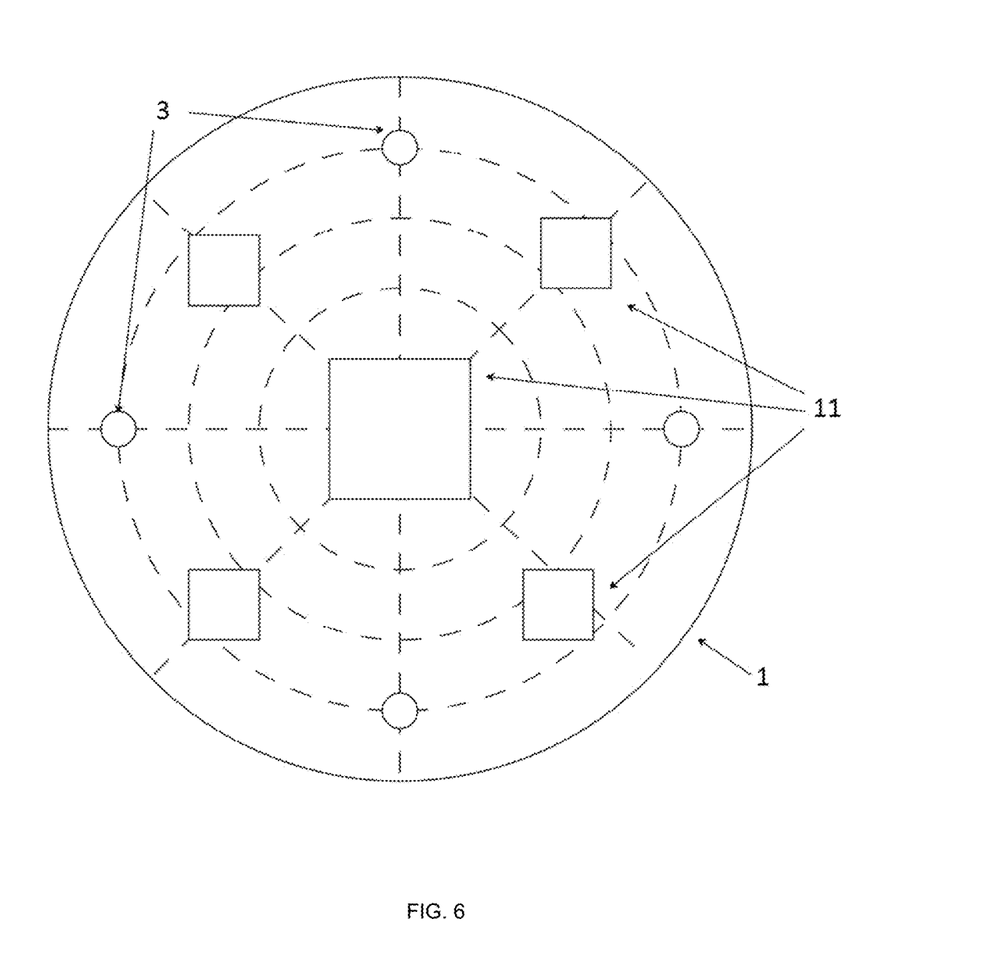
FIG. 6 shows one embodiment of implementation of magnets and solenoid coils/antennas in/on the active implant according to another aspect of the present invention.

To address this issue, and in the attempt of respecting the general wireless nature of the system, in its simplest embodiment, the inclusion of at least one magnetic element 3 within at least one component of the system selected among the active implant 1 or the external reader 2, and a corresponding ferromagnetic element 3' on the other component, previously aligned (e.g. in the manufacturing process of the system) with the above-mentioned magnet 3 has been envisioned, see FIGS. 1 and 2. The magnet 3 can have any suitable shape and dimension as long as it remains able to fix and align the system component it is placed in/on with the other, corresponding one; for instance, a magnet 3 can be embedded within or attached on the bottom surface of the external reader 2 and a ferromagnetic element 3' can be embedded within or attached on the upper surface of the implant 1 and vice versa, said magnetic element having any shape such as a round shape, cross-like shape, squared shape and so forth. This fixing and alignment coupling is obtained by magnets and ferromagnetic elements that interact among them through at least two anchor points. In some embodiments, more than one magnetic element 3 and/or more than one ferromagnetic element 3' can be present in the components of the system; for example, several (e.g., four) round magnetic elements 3 can be present in the external reader 2 and several corresponding ferromagnetic elements 3' can be present in the implant 1. In another embodiment, a magnetic element 3 having any arbitrary shape can placed on or in the edges of the implant 1, while several smaller ferromagnetic elements 3' can be placed in or on the external reader 2. A skilled person can easily envisage many different solutions and topologies for the magnets/ferromagnetic elements to be paired and included into the system's components, some exemplary and non-limiting embodiments of which are depicted in FIGS. 5 and 6.

However, the proposed fixing and alignment solution aims at the wireless connection of the functional active elements of the components of the system, as well as to their optimization in terms of data communication and power transfer. Such optimization is principally obtained thanks to the spatial calibration of said functional active components among them, notably for solenoid coils 12-12' and antennas 11-11'. In view of this, according to one aspect of the present invention, the magnetic elements 3 and the ferromagnetic elements 3' are designed and placed into/onto the implant 1 or the external reader 2 in order to have a misalignment that reduces as much as possible data communication and power transfer leakage. In order to do that, many parameters must be taken into consideration, which are well known in the art; a complete overview on the argument can be found in Kilinc, E. G. at al., Biomedical Circuits and Systems, IEEE Transactions on, vol. 9, no. 1, pp. 113-123, February 2015, this publication being herewith incorporated by reference in its entirety.

Moreover, the magnetic elements 3 and the ferromagnetic elements 3' are designed and arranged in the system components in order to avoid any possible reciprocal permutation, intended as any of the various ways in which a set of things can be ordered, such as rotation and/or translation, once coupled.

As used herein, a "ferromagnetic element" is any material or object that is attracted by the magnetic field produced by a magnet. A "magnet" is any material or object that produces a magnetic field. This definition includes permanent magnets, i.e. an object that creates its own persistent magnetic field, or even electromagnets, a type of magnet in which the magnetic field is produced by an electric current running through closely spaced turns of (usually metallic) wire. Both the magnets and the ferromagnetic materials can be made of elements well-known for their ferromagnetic properties such as iron, nickel, cobalt, rare earth metals such as neodymium or samarium, various kind of alloys or composite thereof such as alnico, ferrite or samarium-cobalt, oxides thereof, naturally-occurring minerals such as lodestone, and many others, as well as any combination of the aforementioned.

Figure 7:
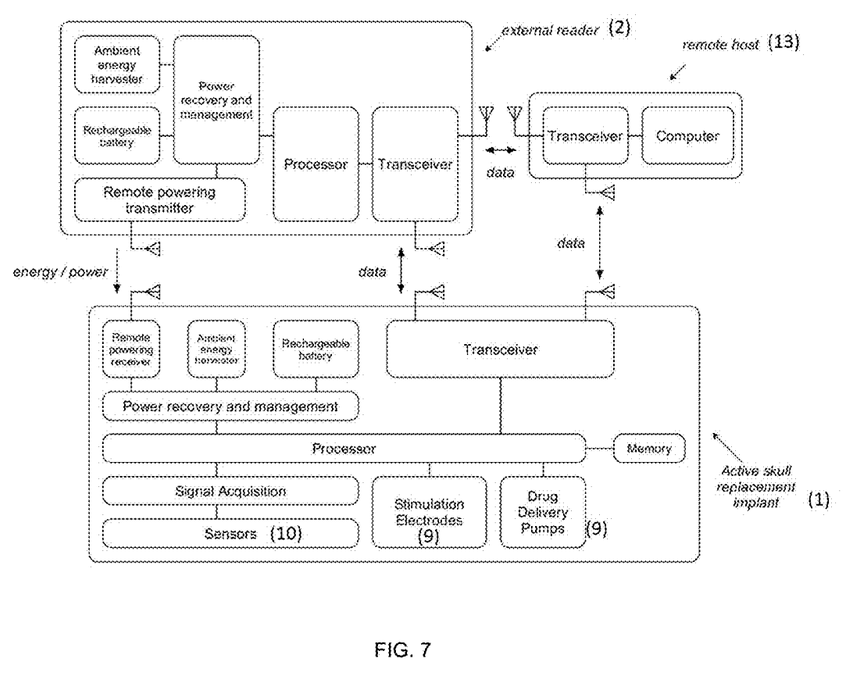
FIG. 7 shows a block diagram of one embodiment of a complete system including a remote host, the active implant and the external reader according to another aspect of the invention.

The system optionally further comprises an external, computer-based remote host 13 operably connected to the implant 1 and/or to the external reader 2 and adapted for communicating with them and/or for collecting, sending, storing and/or processing information concerning a physiological response and/or a physiological parameter of a subject. A block diagram of the complete system including a remote host 13 is depicted on FIG. 7. The remote host 13 is preferably in communication with the external reader 2, and most preferably through wireless means such as WiFi, Bluetooth™, magnetic, radio, telemetric, infrared, optical, ultrasonic connection and the like. The remote host 13 can operate in closed-loop or open-loop mode with the implant 1 and/or to the external reader 2.

Another aspect of the present invention relates to a method or use of the above system for the treatment, diagnosis, monitoring and/or prevention of a disorder of the Central Nervous System (CNS) in a subject, preferably the brain and its associated structures. As used herein, "treatment", "treating" and the like generally mean obtaining a desired pharmacological and/or physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" or "treating" as used herein covers any treatment of a disease in a mammal, particularly a human, and includes: (a) inhibiting the disease, i.e., arresting its development; or (b) relieving the disease, i.e., causing regression of the disease and/or its symptoms or conditions such as improvement or remediation of damage. In particular, treatment of disorders of the CNS comprises, depending on the disorder at issue, to normalize or improve somatic symptoms such as seizures, tremors, chronical infections, dementia, memory loss, intracranial pressure elevation, headache, pain, loss of feeling, loss of muscle strength, hallucinations, increased reflexes, spasticity, slurred speech, tics, paralysis, mood alterations including for instance depression, mania, euphoria and the like, phobias and so forth. As used herein, the term "prevention" or "preventing" relates to hampering, blocking or avoid a disease from occurring in a subject which may be, for any reason, predisposed to the disease but has not yet been diagnosed as having it for example based on familial history, health status or age.

In a non-limiting example, the system can be used in a method for treating, diagnosing, monitoring and/or preventing signs and/or symptoms associated to a pathological conditions of a mammal, preferably a human being, such as Huntington's disease, Parkinson's disease and secondary parkinsonism, epilepsy, ataxias, dyskinesias, degenerative disorders of nervous system including multiple sclerosis, migraines, ischaemic attacks and related syndromes, sleep disorders, pathological conditions due to traumas, poisoning, infections, head surgery, head lesions or congenital issues and the like.

In a non-limiting example, the system can include an active implant 1 surgically implanted into an aperture of the skull 200 of a human patient suffering of epileptic seizures. It is generally preferable to be able to detect and treat a seizure at or near its beginning, or even before it begins. The beginning of a seizure is referred to herein as an "onset." A "clinical onset" represents the beginning of a seizure as manifested through observable clinical symptoms, such as involuntary muscle movements or neurophysiological effects such as lack of responsiveness while an "electrographic onset" refers to the beginning of detectable electrographic activity indicative of a seizure. An electrographic onset will frequently occur before the corresponding clinical onset, enabling intervention before the patient suffers symptoms, but that is not always the case. In addition, there are changes in the EEG that occur seconds or even minutes before the electrographic onset that can be identified and used to facilitate intervention before electrographic or clinical onsets occur. This capability would be considered seizure prediction, in contrast to the detection of a seizure or its onset.

The implant 1 is operably coupled with cortical electrodes 9 through soft wires 8. Electrodes 9 may be of any well-known state-of-the-art EEG type implanted directly over the most opportune areas of the cerebral cortex as determined by preoperative EEG observation adapted for detecting ictal (i.e. seizure) activity. The electrodes 9 can be connected to an electrode interface placed in the implant 1 preferably capable of selecting each electrode as required for sensing. The electrode interface is coupled to a detection subsystem that may include an EEG analyzer adapted to receive EEG signals from the electrodes 9, through the electrode interface, and to process those EEG signals to identify neurological activity indicative of a seizure, an onset of a seizure, or a precursor to a seizure. The EEG analyzer may further possibly record EEG signals, and create a log of such an analysis for providing data useful in the diagnosis or the treatment of epilepsy. Additionally or alternatively, an EEG analyzer can be included in the external reader 2 wirelessly communicating with the electrode interface placed in implant 1 via a transceiver and, in some embodiments, to an external host 13.

The implant 1 can be configured to begin recording all or some of the detected EEG signals from the patient at the onset or as a result of a prediction of ictal activity and to continue recording until the ictal activity stops, and optionally, to save such a recording, or a sampling of it, to a memory device placed therein. For example, but without limitation, the active implant 1 can be configured to record or log the date and time when each such event begins and ends, the duration of the event, indications of the intensity of the event and so forth. Additionally or alternatively, the gathered information can be wirelessly transferred and then stored in a memory device comprised in the external reader 2 and, in some embodiments, to an external host 13.

While the invention has been disclosed with reference to certain preferred embodiments, numerous modifications, alterations, and changes to the described embodiments, and equivalents thereof, are possible without departing from the sphere and scope of the invention. Accordingly, it is intended that the invention not be limited to the described embodiments, and be given the broadest reasonable interpretation in accordance with the language of the appended claims.

The invention claimed is:

1. An active skull replacement system comprising:
an implant having an area A, an upper surface, and a bottom surface, adapted to be implanted at least in part into a skull of a subject so to substitute a portion of the skull, the bottom surface arranged to face at least in part a cranial cavity, and having a first wireless bidirectional data communication device;
a device operably connected to the bottom surface of the implant, the device adapted to at least one of stimulate a physiological response and record a physiological parameter of the subject; and
an external reader adapted to be placed on the scalp of the subject and including a second wireless bidirectional data communication device configured to communicate with the first wireless bidirectional data communication device of the implant to operate the device,
wherein the external reader and the implant are fixed and aligned among each other through a magnetic device, and
wherein the area A is adapted to dissipate the heat generated by at least one of the device and the implant.

2. The system of claim 1, wherein the first wireless bidirectional data communication device includes an antenna in the implant and the second wireless bidirectional data communication device includes an antenna in the external reader.

3. The system of claim 2, wherein the antennas of the implant and the external reader are aligned between each other through the magnets.

4. The system of claim 1, wherein the external reader comprises a remote powering device for powering of the implant.

5. The system of claim 4, wherein the remote powering device operates with magnetic coupling of solenoid coils, the solenoid coils operably placed in the implant and the external reader.

6. The system of claim 5, wherein the magnets in the implant and the external reader are placed in a center of, respectively, the solenoid coil in the implant and the solenoid coil in the external reader, so to align them with each other along their respective long axis.

7. The system of claim 2, wherein the solenoid coil and the antenna in each of the implant and the external reader of the system independently have a 90° orientation between each other.

8. The system of claim 2, wherein the area A of the implant is $((\sqrt{N}+(\sqrt{N}-1))^2) \times x^2$, wherein x is the diameter of the antenna of the implant and N is a number of antennas.

9. The system of claim 1, wherein the device operably connected to the bottom surface of the implant includes at least one selected from the group consisting of an electrocorticography electrode, an array of electrocorticography electrodes, active/passive microelectrode arrays with stimulation/recording capabilities, a deep brain stimulation electrode, an array of deep brain stimulation electrodes, a drug delivery device, a chemical sensor, a temperature sensor, and a pressure sensor.

10. The system of claim 1, further comprising:

a computer-based remote host operably connected to at least one of the implant and to the external reader and adapted for communicating with the at least one of the implant and the external reader.

11. The system of claim 1, further comprising:

a computer-based remote host operably connected to at least one of the implant and to the external reader and adapted to at least one of collect, send, store, and process information concerning a physiological response.

12. The system of claim 1, further comprising:

a computer-based remote host operably connected to at least one of the implant and to the external reader and adapted to at least one of collect, send, store, and process information concerning a physiological parameter of the subject.

* * * * *